United States Patent [19]

Feingold

[11] Patent Number: 5,499,987
[45] Date of Patent: Mar. 19, 1996

[54] DEFORMABLE INTRAOCULAR LENS CARTRIDGE

[75] Inventor: Vladimir Feingold, Laguna Niguel, Calif.

[73] Assignee: Staar Surgical Company, Monrovia, Calif.

[21] Appl. No.: 197,604

[22] Filed: Feb. 17, 1994

Related U.S. Application Data

[63] Continuation-in-part of Ser. No. 953,251, Sep. 30, 1992, abandoned.

[51] Int. Cl.⁶ .................................................. A61B 17/00
[52] U.S. Cl. ........................... 606/107; 623/6; 206/5.1
[58] Field of Search ............................... 623/6; 606/107; 206/5.1

[56] References Cited

U.S. PATENT DOCUMENTS

| | | | |
|---|---|---|---|
| 4,681,102 | 7/1987 | Bartell | 606/107 |
| 4,919,130 | 4/1990 | Stoy et al. | |
| 5,123,905 | 6/1991 | Kelman | |
| 5,190,552 | 3/1993 | Kelman | |
| 5,275,604 | 1/1994 | Rheinish et al. | 606/107 |
| 5,304,182 | 4/1994 | Rheinish | 623/6 X |

OTHER PUBLICATIONS

One (1) sheet of drawings of prior art device sold by Staar Surgical Company of Monrovia, CA.

Primary Examiner—Mary Beth O. Jones
Attorney, Agent, or Firm—Klima & Hopkins

[57] ABSTRACT

An improved lens cartridge for use in a lens injecting device. The lens cartridge and lens injecting device define a surgical implantation device for inserting a deformable intraocular lens into the eye through a relatively small incision made in the ocular tissue. A preferred lens cartridge comprises a lens holding portion connected to a nozzle portion with a passageway extending therethrough, and including at least one groove in the passageway. Another preferred embodiment comprises a lens holding portion connected to a nozzle portion with an inwardly tapering passageway extending therethrough. A further preferred embodiment includes both the passageway groove feature and the inwardly tapering passageway feature.

57 Claims, 11 Drawing Sheets

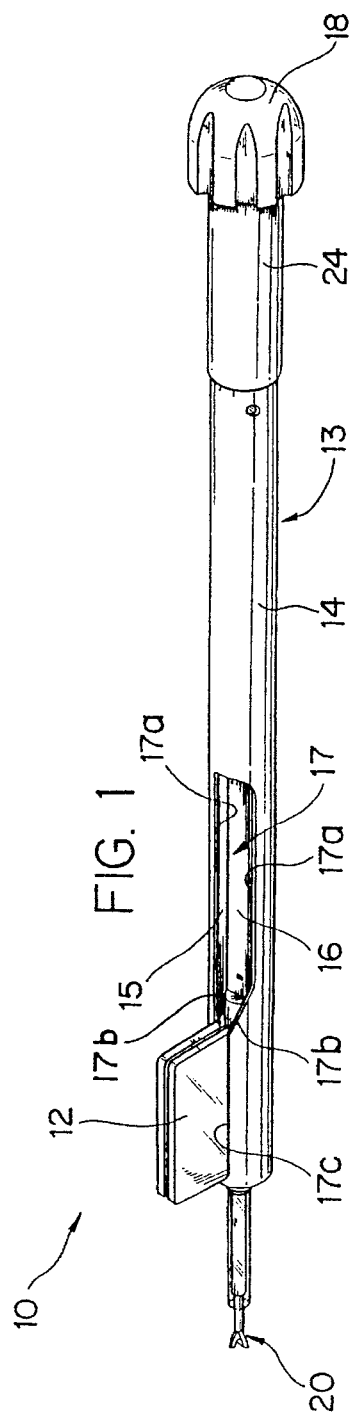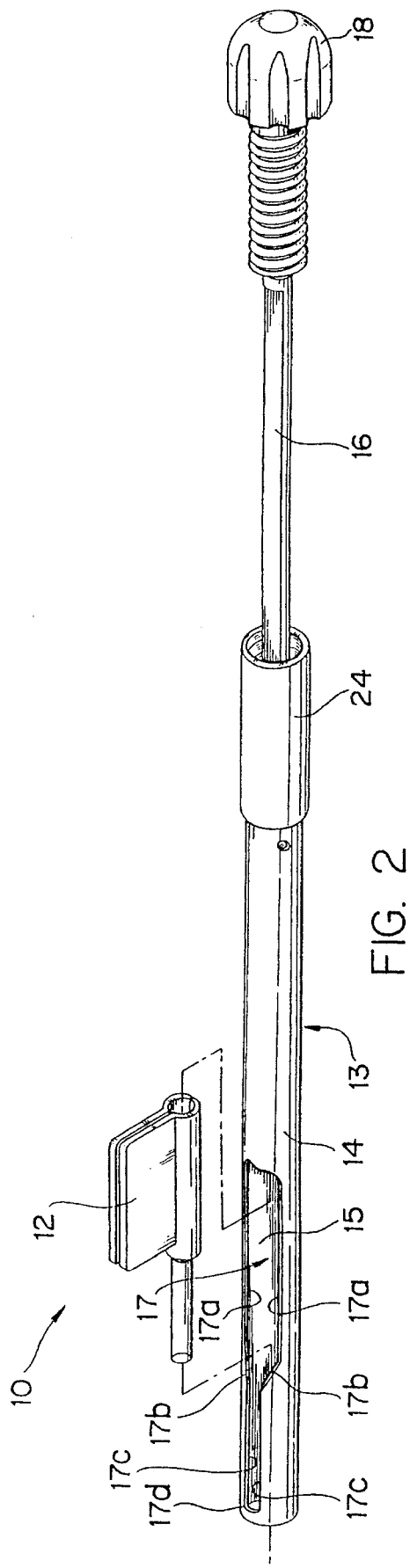

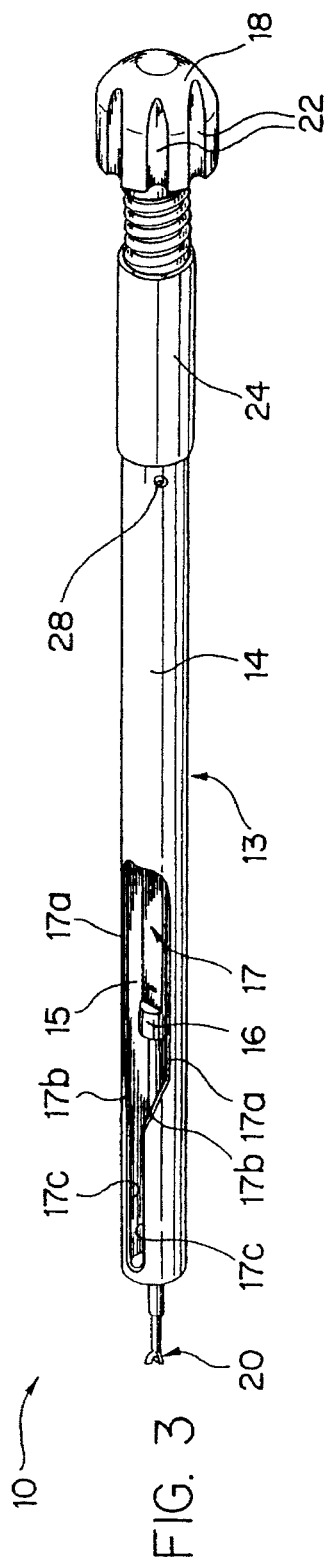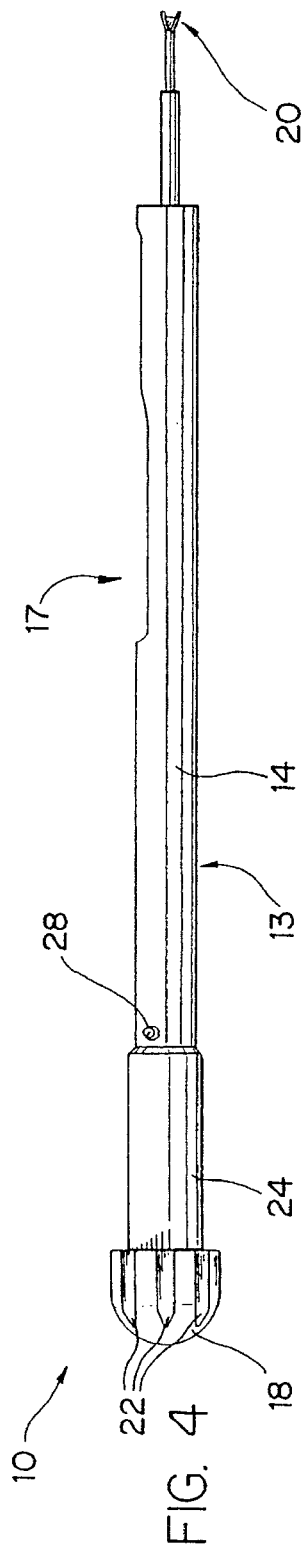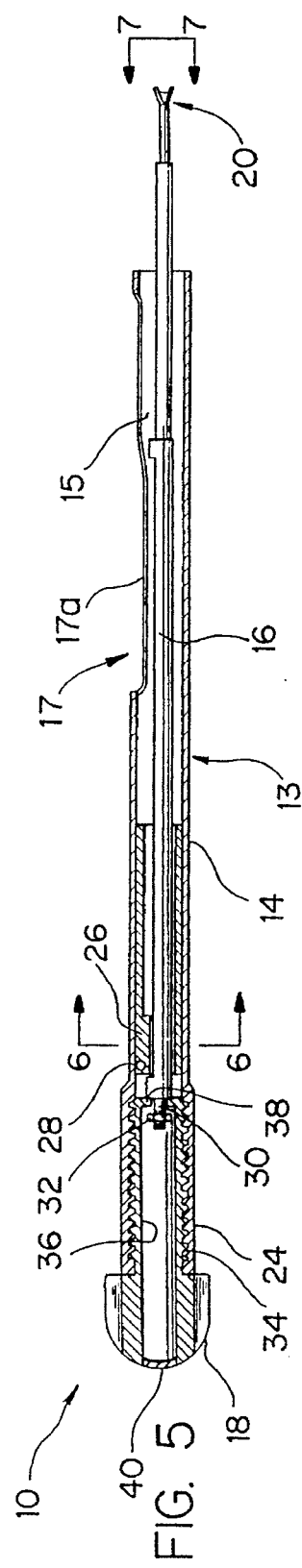

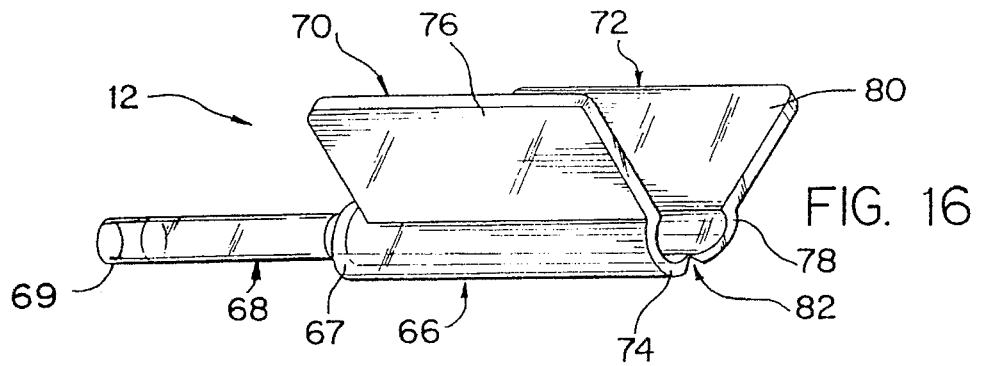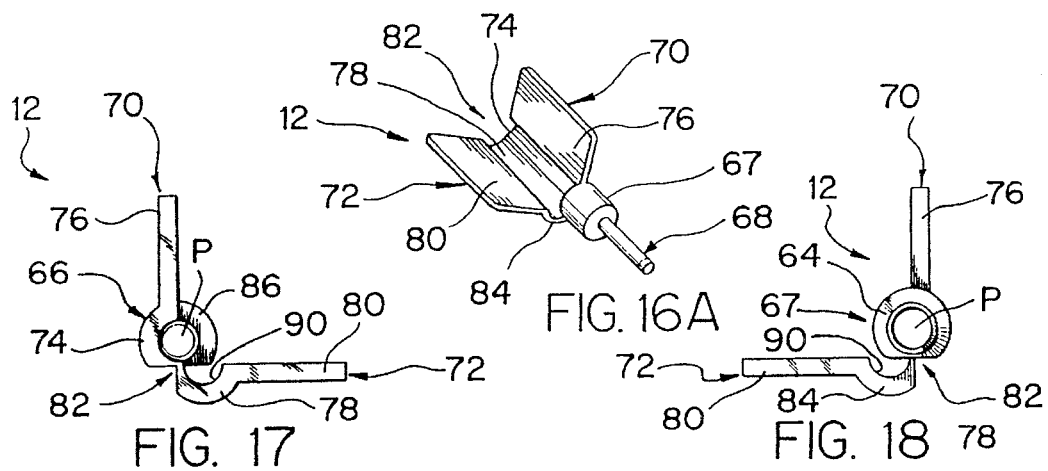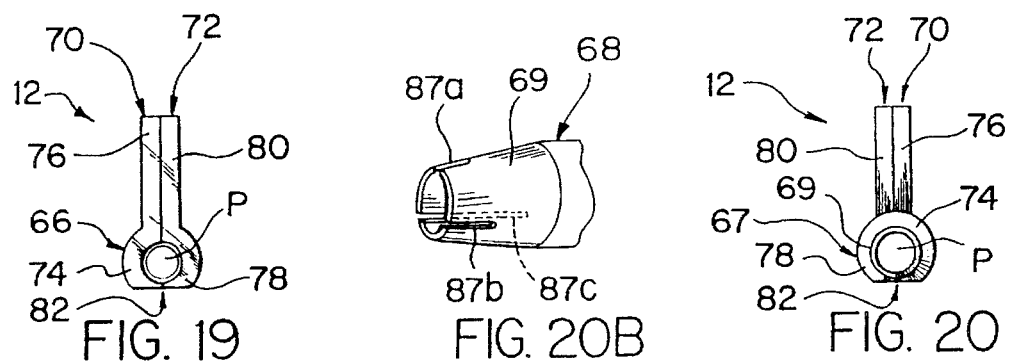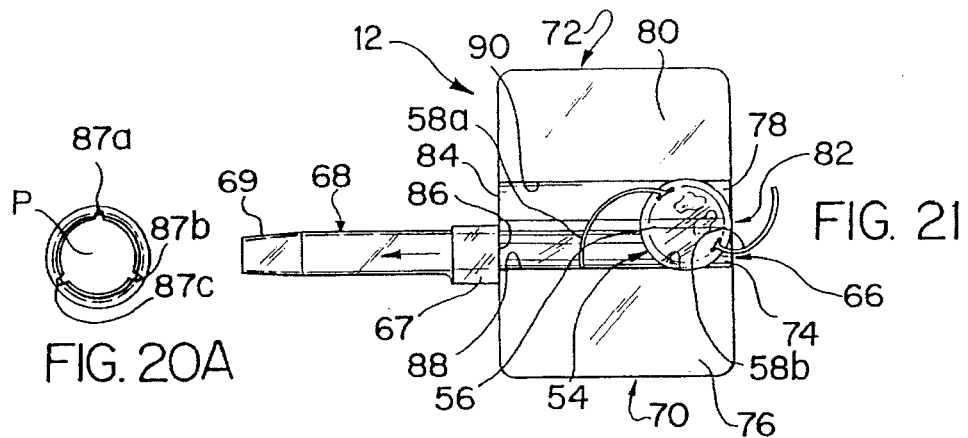

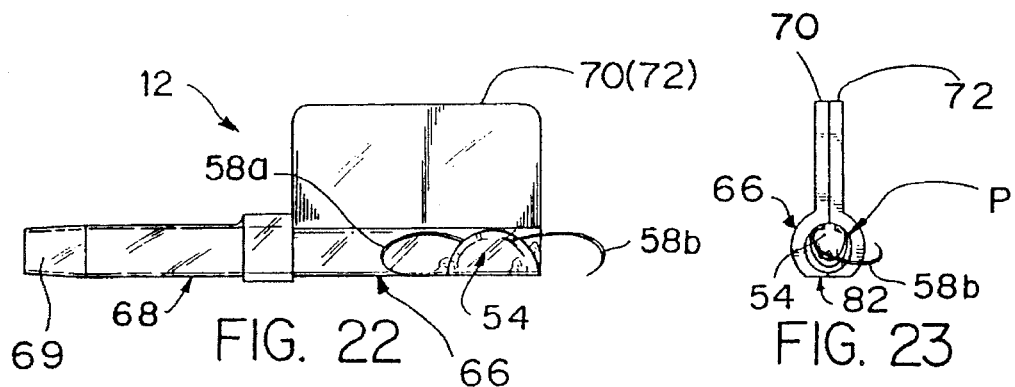
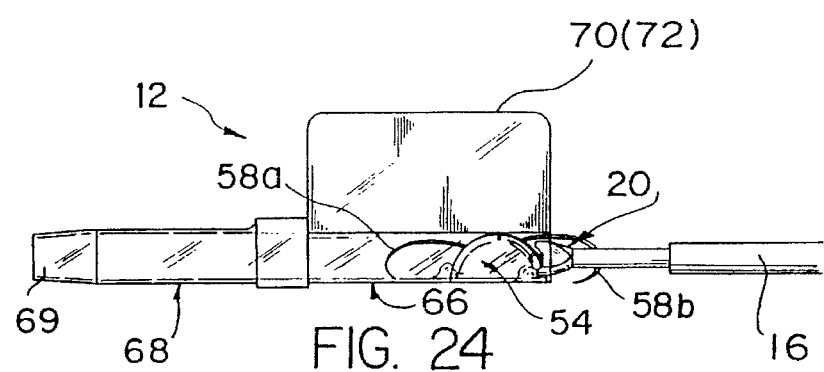
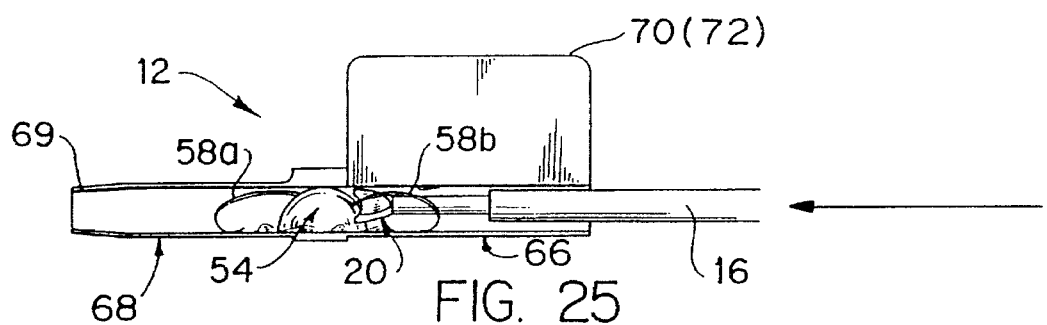
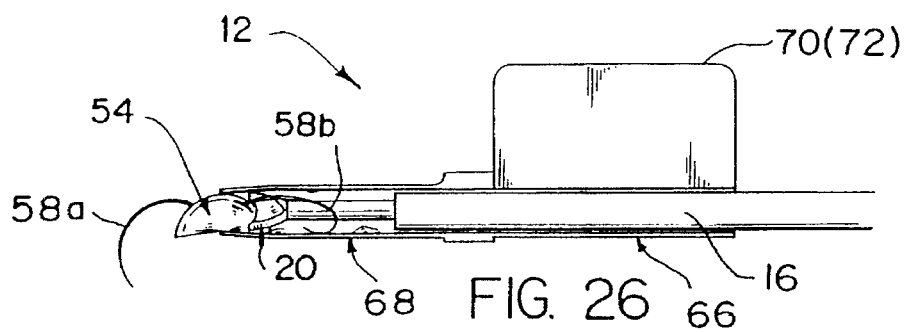

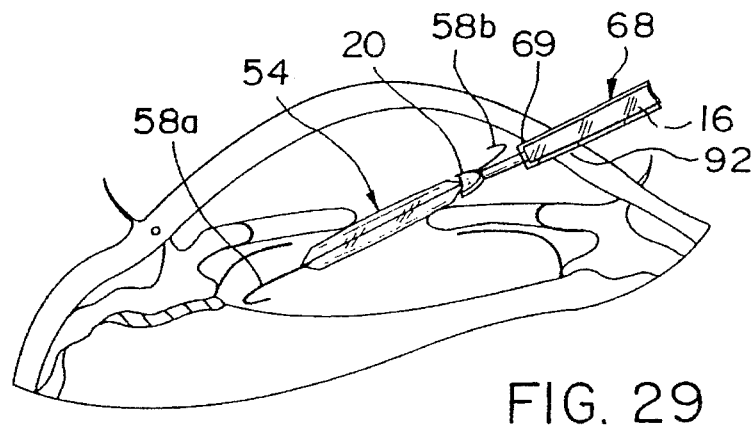
FIG. 29
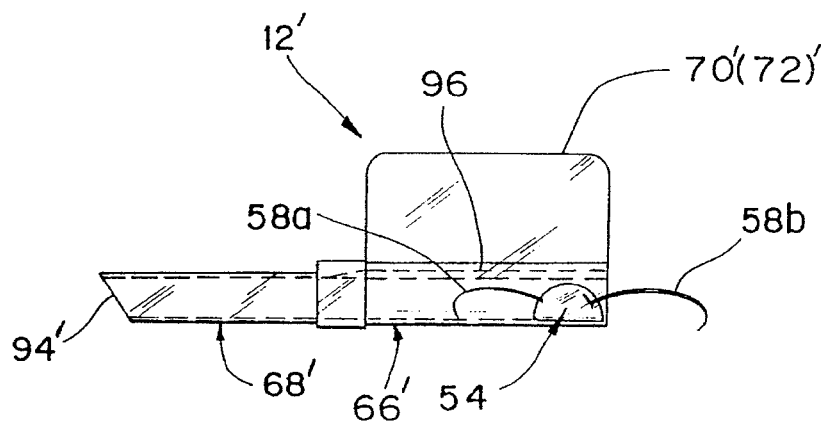
FIG. 30
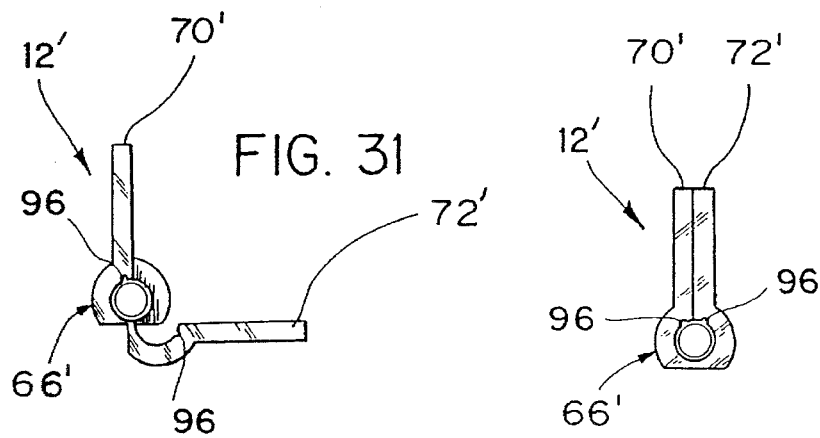
FIG. 31
FIG. 32
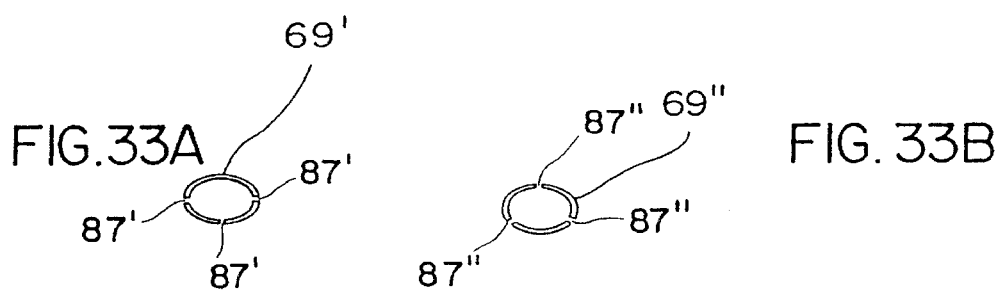
FIG. 33A
FIG. 33B

DEFORMABLE INTRAOCULAR LENS CARTRIDGE

CROSS REFERENCE TO RELATED APPLICATION

This application is a continuation-in-part application of U.S. patent application Ser. No. 07/953,251, filed on Sep. 30, 1992, now abandoned.

BACKGROUND OF THE INVENTION

1. Field of the Invention

This invention relates to improved lens cartridges for use with surgical instruments for the implantation of deformable intraocular lenses into the eye.

2. Prior Art

Intraocular lenses have gained wide acceptance in replacement of human crystalline lenses after a variety of cataract removal procedures. The human crystalline lens is generally recognized to be a transparent structure having a thickness of about five (5) millimeters and a diameter of about nine (9) millimeters. The lens is suspended behind the iris by zonula fibers which connect the lens to the ciliary body. A lens capsule surrounds the lens, the front portion of the capsule being commonly known as the anterior capsule and the back portion commonly known as the posterior capsule.

Numerous procedures for the removal of cataracts have been developed in which the lens is removed from the eye and replaced by an artificial lens implant. The extraction procedure may generally be categorized as intracapsular (in which the lens is removed together with the lens capsule) and extracapsular (in which the anterior capsule is removed with the lens, and the posterior capsule is left intact).

Since Ridley implanted the first artificial lens in about 1949, the problems associated with cataract extraction and lens implantation have received a great deal of attention from ophthalmic surgeons. Various types of artificial lenses have been proposed, and appropriate surgical procedures have been developed which strive to reduce patient discomfort and to reduce postoperative complications. Reference is made in this connection to Pseudophakos by N. Jaffe et al., "History of Intraocular Implants" by D. P. Choyce (Annals of Ophthalmology, October 1973); U.S. Pat. No. 4,251,887 issued to Anis on Feb. 24, 1981; U.S. Pat. No. 4,092,743 issued to Kelman on Nov. 8, 1977; "Comparison of Flexible Posterior Chamber Implants", presented at the American Intraocular Implant Society Symposium Apr. 23, 1982, by Charles Berkert, M.D.; and "the Simcoe Posterior Lens" (Cilco, Inc. 1980); U.S. Pat. No. 4,573,998 issued to Mazzocco on Mar. 4, 1986, U.S. patent application Ser. No. 400,665 for "Improved Fixation System for Intraocular Lens Structures", filed Jul. 22, 1982, U.S. Pat. No. 4,702,244 issued to Mazzocco on Oct. 27, 1987; and U.S. Pat. No. 4,715,373 issued to Mazzocco et al. on Dec. 29, 1987, which disclosures are hereby incorporated by reference.

Of particular interest in the context of the present invention is the development of surgical techniques requiring relatively small incisions in the ocular tissue for the removal of cataracts as disclosed in U.S. Pat. Nos. 4,002,169 and 3,996,935. A number of skilled artisans have disclosed intraocular lens structures comprising an optical zone portion generally made of rigid materials such as glass or plastics suitable for optical use.

However, one of the principal disadvantages of the conventional rigid intraocular lens is that implantation of the lens requires large incisions in the ocular tissue. This type of surgical procedure leads to a relatively high complication rate, among other disadvantages. For instance, the serious dangers associated with implantation of a rigid lens structure include increased risk of infection, retinal detachment, and laceration of the ocular tissue, particularly with respect to the pupil.

Accordingly, those skilled in the art have recognized a significant need for surgical tools for implantation of deformable intraocular lens structures which afford the clinical advantages of using relatively small incision techniques, which provide a safer and more convenient surgical procedure. In particular, those skilled in the art of deformable intraocular lenses and methods and devices for implantation, have also recognized a significant need for surgical tools which do not require widening of the wound made in the ocular tissue during or after implantation, but will deform the intraocular lens to a predetermined cross section in a stressed state and which allow the ophthalmic surgeon to inspect the lens prior to implantation without manipulation in the eye. The present invention fulfills these needs.

The present invention was derived by improving the methods and devices in the above-identified patents, specifically the methods of U.S. Pat. No. 4,573,998 and the devices of U.S. Pat. No. 4,702,244.

SUMMARY OF THE INVENTION

An object of the present invention is to provide an improved lens cartridge for use with a surgical instrument for implantation of deformable intraocular lenses.

Another object of the present invention is to provide a lens cartridge for use with a surgical lens injecting device for implantation of a deformable intraocular lens into the eye through a relatively small incision made in the ocular tissue, the lens cartridge comprising a lens holding portion, a nozzle portion connected to and extending from the lens holding portion, the lens holding portion and the nozzle portion having a continuous passageway extending therethrough, the passageway having at least one groove extending along at least a portion of the length of the passageway for manipulating the deformable intraocular lens as it passes through the lens cartridge.

A further object of the present invention is to provide a lens cartridge for receiving a lens comprising a split tubular member having a fixed portion with an extension, and a movable portion with an extension for opening and closing the lens cartridge, which extensions prevent rotation between the lens cartridge and lens injecting device when installed in the lens injecting device.

An even further object of the present invention is to provide a lens cartridge having a nozzle portion provided with slots for rotating the lens as it exits the nozzle portion.

Another further object of the present invention is to provide a surgical implantation device comprising a lens cartridge and a lens injecting device, the lens injecting device comprising a receiver for the lens cartridge and a plunger for inserting the deformable intraocular lens.

Another object of the present invention is to provide a lens cartridge defined by a cylindrical tubular member with an opening through the wall of the tubular member defining a receiver for the lens cartridge, and a plunger having a tip for contacting with and moving a deformable intraocular lens contained in the lens cartridge.

A further object of the present invention is to provide a plunger with a faceted tip that provides clearance for a trailing haptic in a passageway through the lens cartridge during the implantation process to prevent damage to the trailing haptic.

An even further object of the present invention is to provide a plunger having a tip with a concave conical surface at the tip thereof for grabbing the lens during the implantation process.

Another further object of the present invention is to provide improved methods of implanting deformable intraocular lenses.

Another object of the present invention is to provide a method including loading a deformable intraocular lens into a lens cartridge having an implantation nozzle, condensing the intraocular lens within the lens cartridge, and implanting the lens into the eye.

The present invention concerns methods and devices for implantation of intraocular lenses into the eye, in particular improved microcartridges.

The surgical implantation device according to the present invention includes the combination of a lens cartridge and a lens inserting or injecting device for holding the lens cartridge. The preferred lens cartridge comprises the combination of a lens holding portion and an implantation nozzle portion. The lens holding portion is preferably defined by a split tubular member having a fixed tubular portion with an extension connected to a movable tubular portion with an extension, at a hinge. This configuration allows the lens cartridge to be opened to accept a deformable intraocular lens, and closed to condense the deformable intraocular lens into the passageway. The lens holding portion is connected to the nozzle portion with a continuous passageway passing through the lens holding portion and the nozzle portion.

The lens cartridge is inserted into the lens injecting device having means for driving or manipulating the deformable intraocular lens from the lens cartridge into the eye. In the preferred embodiment, the lens injecting device is provided with a plunger for driving the deformable intraocular lens from the lens cartridge into the eye. Further, the lens injecting device is configured to receive a lens cartridge having a nozzle portion.

The preferred lens injecting device includes means to prevent the lens cartridge from rotating within the lens injecting device, and means for preventing the plunger from rotating within the lens injecting device. The means for preventing rotation of the lens cartridge within the lens injecting device can be defined by providing the lens cartridge with one or more extensions that cooperate with the opening of the lens cartridge receiver of the lens injecting device to prevent rotation. The means for preventing the plunger from rotating within the lens injecting device can be defined by providing both the plunger and a sleeve within the lens injecting device with a particular cross-sectional shape that prevents relative rotation, for example, a half-circle shape.

The preferred lens injecting device includes a plunger with a threaded cap cooperating with a threaded sleeve of the body of the lens injecting device for dialing the plunger forward within the lens injecting device for precise and accurate movement of the lens during the implantation process. The lens injecting device is configured so that the plunger can be moved a predetermined distance by sliding motion within the body of the lens injecting device followed by engagement of the threaded cap of the plunger with the threaded sleeve of the body of the lens injecting device to continue the forward progress of the plunger tip.

The preferred plunger tip is defined by a faceted tip having various surfaces for moving and manipulating the lens from the lens cartridge and within the eye. The tip is designed to provide a clearance between the tip and the inner surface of the passageway through lens cartridge to accommodate the trailing haptic and prevent damage thereto. Once the lens is inserted into the eye, the tip can be used to push and rotate the lens into proper position within the eye.

A method according to the present invention includes lubricating the surface of a deformable intraocular lens with a surgically compatible lubricant, and loading the lens into a lens cartridge in the opened position. The lens cartridge is closed while condensing the lens by a folding action into a shape so that it can be forced through the passageway in the lens cartridge. The lens cartridge is inserted into the lens injecting device with the plunger retracted.

The plunger is moved forward in a sliding manner by pushing the plunger forward while holding the body of the lens injecting device still. This action forces the deformable intraocular lens from the lens holding portion of the lens cartridge into the nozzle portion. At this point the threads of the threaded end cap of the plunger engage with the threads of the threaded sleeve. The threaded end cap is rotated slightly to engage the threads. The device is now ready for the implantation process.

The nozzle of the microcartridge is placed through a small incision in the eye. The threaded end cap of the plunger is rotated or dialed to further advance the lens forward through the nozzle and into the eye. The threaded end cap is further dialed to exposed the tip of the plunger within the eye and push the lens into position. The tip can be used to also rotate the lens within the eye for positioning of the haptics.

BRIEF DESCRIPTION OF THE DRAWINGS

FIG. 1 is a perspective view of one embodiment of the surgical implantation device according to the present invention with a lens holding microcartridge positioned in the lens injecting device for implantation of a deformable intraocular lens into the eye.

FIG. 2 is a perspective view of the surgical implantation device shown in FIG. 1 with the plunger retracted, and with the lens holding microcartridge removed.

FIG. 3 is a side view of the surgical implantation device shown in FIG. 2 with the plunger in the extended position.

FIG. 4 is a side elevational view of the surgical implantation device shown in FIG. 1.

FIG. 5 is a detailed longitudinal cross-sectional view of the surgical implantation device shown in FIG. 4.

FIG. 16 is a perspective view of a lens holding microcartridge shown in the open position to allow a deformable intraocular lens to be loaded therein.

FIG. 16A is another perspective view of the lens holding microcartridge shown in the open position.

FIG. 17 is a rear end elevational view of the lens holding microcartridge shown in the open position.

FIG. 18 is a front end elevational view of the lens holding microcartridge shown in the open position.

FIG. 19 is a rear end elevational view of the lens holding microcartridge shown in the closed position.

FIG. 20 is a front end elevational view of the lens holding microcartridge shown in the closed position.

FIG. 20A is a detailed end view of the nozzle portion showing three (3) slots of different length equally spaced about the circumference of the tip.

FIG. 20B is a detailed perspective view of the tip showing the three (3) slots of different length.

FIG. 21 is a top planar view of the lens holding microcartridge shown in the open position.

FIG. 22 is a side elevational view of the lens holding microcartridge shown in the closed position.

FIG. 23 is a rear end elevational view of the lens holding microcartridge shown in the closed position.

FIG. 24 is a broken away side view of the surgical implantation device showing the lens holding microcartridge in relationship to the plunger in the retracted position.

FIG. 25 is a broken away side view of the surgical implantation device showing the lens holding microcartridge in relationship to the plunger in a partially extended position.

FIG. 26 is a broken away side view of the surgical implantation device showing the lens holding microcartridge in relationship to the plunger in a fully extended position.

FIG. 29 is a cross-sectional view of an eye showing the positioning of the deformable intraocular lens into a different position in the eye by the surgical device.

FIG. 30 is a side elevational view of an alternative embodiment of the lens holding microcartridge provided with a beveled tip.

FIG. 31 is a rear end elevational view of another alternative embodiment of the lens holding microcartridge provided with grooves in the passageway to facilitate folding the deformable intraocular lens in an open position.

FIG. 32 is a rear end elevational view of another alternative embodiment of the lens holding microcartridge provided with grooves in the passageway to facilitate folding the deformable intraocular in a closed position.

FIG. 33A is a front end elevational view of the nozzle portion of an alternative embodiment of the lens holding microcartridge.

FIG. 33B is a front end elevational view of the nozzle portion of a further alternative embodiment of the lens holding microcartridge.

DESCRIPTION OF PREFERRED EMBODIMENTS

Figure 6:
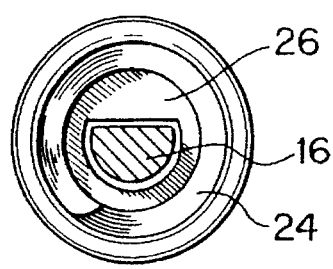
FIG. 6 is a detailed transverse cross-sectional view of the surgical implantation device, as indicated in FIG. 5.
Figure 7:
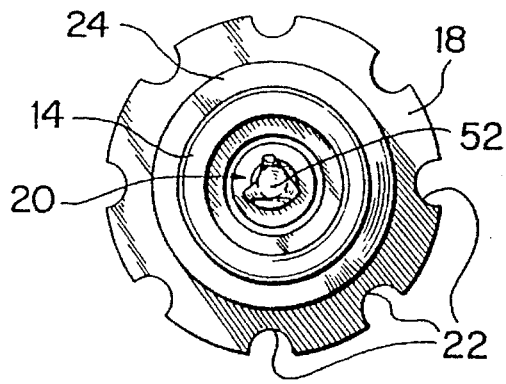
FIG. 7 is a detailed end view of the surgical implantation device, as indicated in FIG. 5.

The present invention is directed to a system including methods and devices for implantation of deformable intraocular lens structures for surgical placement in the eye.

A surgical implantation device according to the present invention comprises a lens injecting device having a lens cartridge receiver, a lens cartridge (e.g., "microcartridge") that can be removably inserted into the lens cartridge receiver of the lens injecting device, and means such as a movable plunger disposed within the lens injecting device to force and manipulate the lens from the lens cartridge into the eye.

Preferably, the lens cartridge is defined by a lens holding microcartridge for receiving the lens structure. Further, the microcartridge is preferably a structure configured to be opened and closed. The preferred embodiment of the microcartridge receives a lens having prescribed memory characteristics when in the open position, and performs the function of folding or deforming the lens structure into a condensed configuration when closed. Alternatively, the microcartridge can be a structure having a passageway defined by a continuous walled annulus, and a lens can be inserted into the passageway from the end of microcartridge by compressing, rolling, folding, or combination of these techniques prior to insertion into the microcartridge.

Once a lens is loaded into the microcartridge, the microcartridge is loaded into the lens injecting device. The assembled surgical implantation device maintains the lens in its condensed configuration during insertion into the eye yet permits the deformed lens to return to its original configuration, size and fixed focal length once implanted in the eye, thereby providing a safe, convenient, and comfortable surgical procedure.

A preferred embodiment of a surgical implantation device 10 according to the present invention is shown in FIGS. 1, 2 and 3. The surgical implantation device 10 comprises a microcartridge 12 (i.e., "lens cartridge") disposed within a lens injecting device 13 comprising a body 14 with a lens cartridge receiver 15, and a movable plunger 16. In FIG. 1, the lens cartridge receiver 15 is defined by an opening 17 through the wall of the body 14 of the size and shape shown in FIGS. 1 and 2. The opening 17 is defined by parallel edges 17a, 17a, which are sufficiently spaced apart to allow the microcartridge 12 to be loaded into the lens cartridge receiver 15 of the lens injecting device 13, tapered edges 17b, 17b, clamping edges 17c, 17c, and stop edge 17d. In FIG. 1, the microcartridge 12 is positioned in the receiver 15 between the clamping edges 17c, 17c with the plunger 16 extending through the microcartridge 12 in a position, for example, after a lens implantation procedure.

In FIG. 2, the lens holding microcartridge 12 is shown removed from the lens injecting device 13 with the plunger 16 in a retracted position for allowing the microcartridge 12 containing a loaded lens and its haptics to be inserted within the lens injecting device 13. In FIG. 3, the lens injecting device 13 is shown with the plunger 16 in the extended position without the microcartridge 12 for purposes of illustration of the components.

The plunger 16 is fitted with a threaded end cap 18 at one end, and fitted with a tip 20 at an opposite end. The threaded end cap 18 is provided with a plurality of grooves 22 to allow a person to tightly grip the cap 18 with his or her finger tips. The threaded end cap 18 is received within a threaded sleeve 24 of the body 14. The threaded end cap 18 can be a separate component attached to the lens injecting device 13, or integral therewith, as shown in the construction in FIG. 5.

The plunger 16 is installed within the lens injecting device 13 in a manner to allow the plunger to be reciprocated therein. In the illustrated embodiment, the plunger 16 is supported for sliding movement within the lens injecting device 13 by guide 26, as shown in FIGS. 5 and 6. The outer dimension of the guide 26 is approximately the same size as the inner dimensions of the lens injecting device 13 to allow the guide to be inserted within the lens injecting device 13. During construction, the guide 26 is inserted within the lens injecting device 13, and locked into position by pin 28 inserted into a predrilled hole in both the wall of the lens injecting device 13 and guide 26.

The cross-sectional shape of the plunger 16 as well as the shape of the inner surface of the guide 26 are approximately a half-circle, as shown in FIG. 6. This arrangement prevents the plunger 16 from rotating within the lens injecting device 13 to maintain the orientation of the tip 20 relative to the lens injecting device 13 during operation.

The threaded end cap 18 is connected to the plunger 16 in a manner to allow the threaded end cap 18 to be rotated relative to the plunger 16. For example, the left end of the plunger 16 (FIG. 5) is provided with a threaded extension 30, which is secured to the threaded end cap 18 by a nut 32. Specifically, the threaded end cap 18 is manufactured with external threads 34 and a longitudinal center bore 36 that ends on the right side of the threaded end cap 18 leaving an end wall 38.

The end wall 38 is provided with a hole slightly larger than the outer diameter of the threaded extension 30 to allow the threaded end cap 18 to freely rotate on the plunger 16 while being secured to the end of the plunger 16. During construction, the nut 32 is inserted through the center bore 36 and threaded onto the threaded extension 30 to secure the threaded end cap 18 to the plunger 16. A curved end cap 40 is press fitted into the end of the center bore 36 to seal the center bore 36 and prevent debris from entering therein during use.

Figure 8:
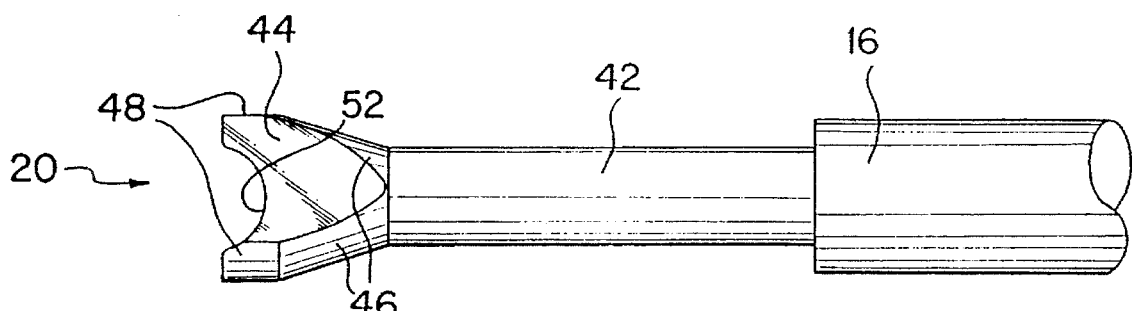
FIG. 8 is an enlarged detailed left side elevational view of the tip of the plunger in the spatial orientation as shown in FIG. 1.
Figure 9:
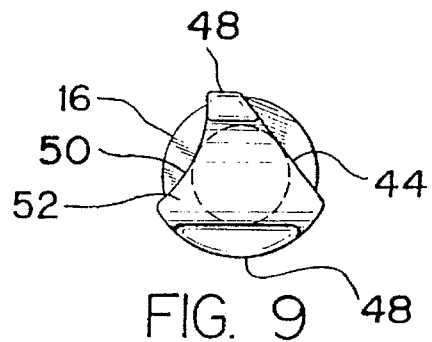
FIG. 9 is an enlarged detailed end view of the tip shown in FIG. 8.
Figure 10:
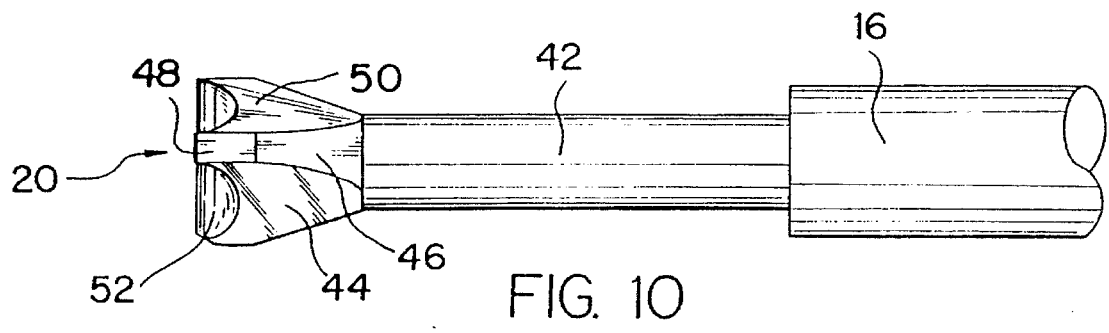
FIG. 10 is an enlarged detailed top planar view of the tip of the plunger.
Figure 11:
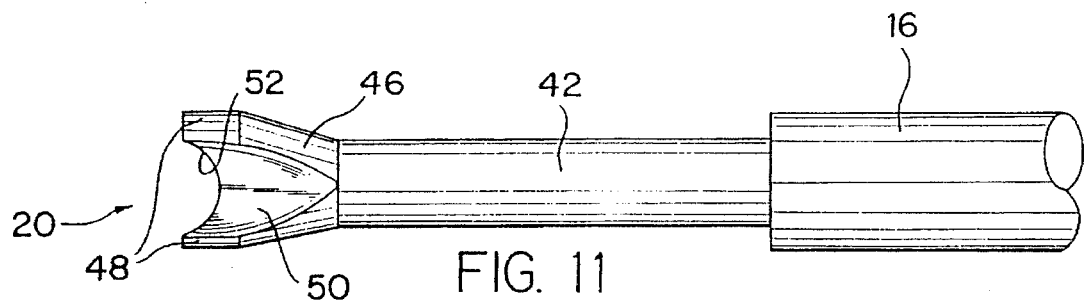
FIG. 11 is an enlarged detailed right side elevational view of the tip of the plunger in the spacial orientation, as shown in FIG. 4.
Figure 12:
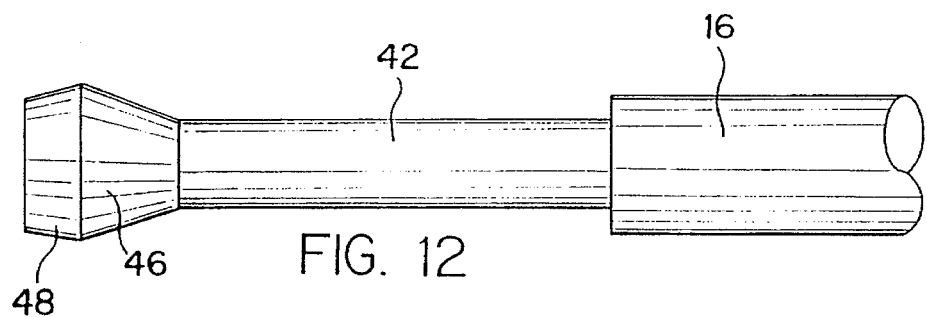
FIG. 12 is an enlarged detailed bottom view of the tip of the plunger in the spacial orientation, as shown in FIG. 1.

The details of the tip arrangement are shown in FIGS. 7 to 12. The plunger 16 is manufactured with an extension 42 supporting tip 20. The tip 20 structure provides means for inserting the deformable intraocular lens into the eye and manipulating the lens within the eye after the insertion step. For example, the tip 20 is faceted in the manner shown in the figures. Specifically, the left side of the tip 20 shown in FIG. 8 is provided with a flat surface facet, 44 conical surface 46, and cylindrical surface 48. The right side of the tip 20 shown in FIG. 11 is provided with a concave surface facet 50.

The end face of the tip 20 is designed to push the lens into position once inserted into the eye. For example, the end face is defined by a concave cylindrical surface 52 shown in FIG. 8.

Figure 13:
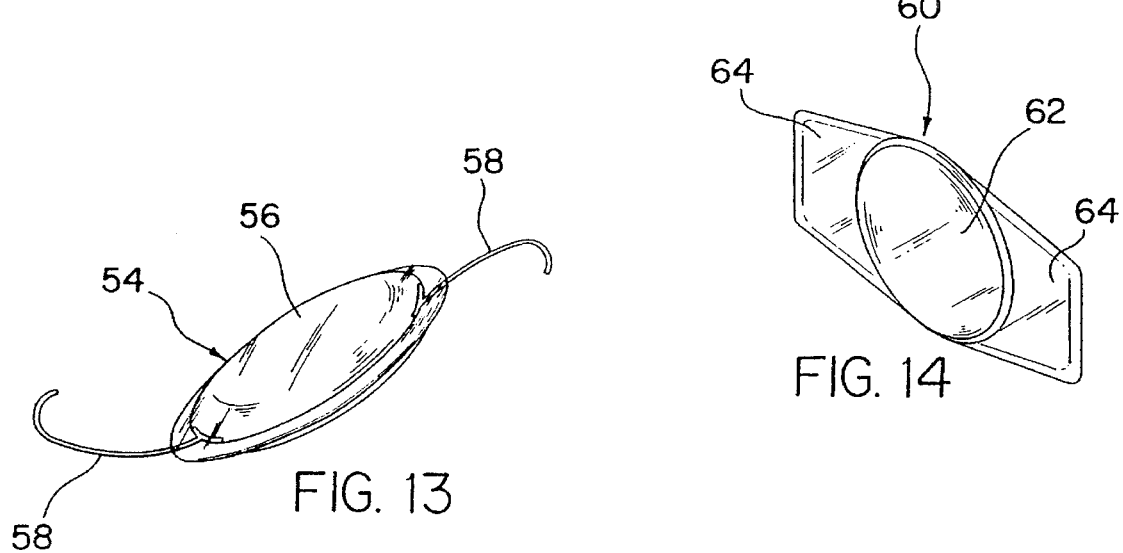
FIG. 13 is a perspective view of a deformable intraocular lens for use in the present invention.
Figure 14:
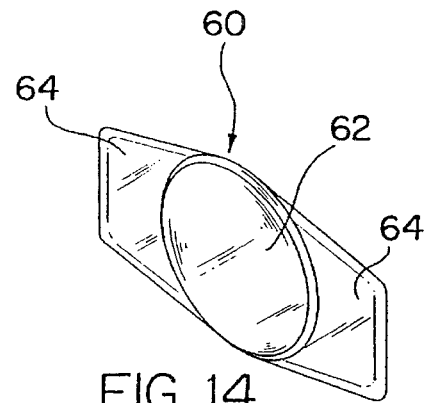
FIG. 14 is a perspective view of another type of deformable intraocular lens for use in the present invention.
Figure 15:
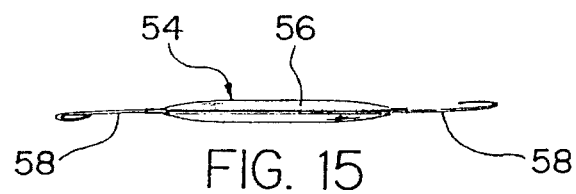
FIG. 15 is a side view of the deformable intraocular lens shown in FIG. 13.
Figure 27:
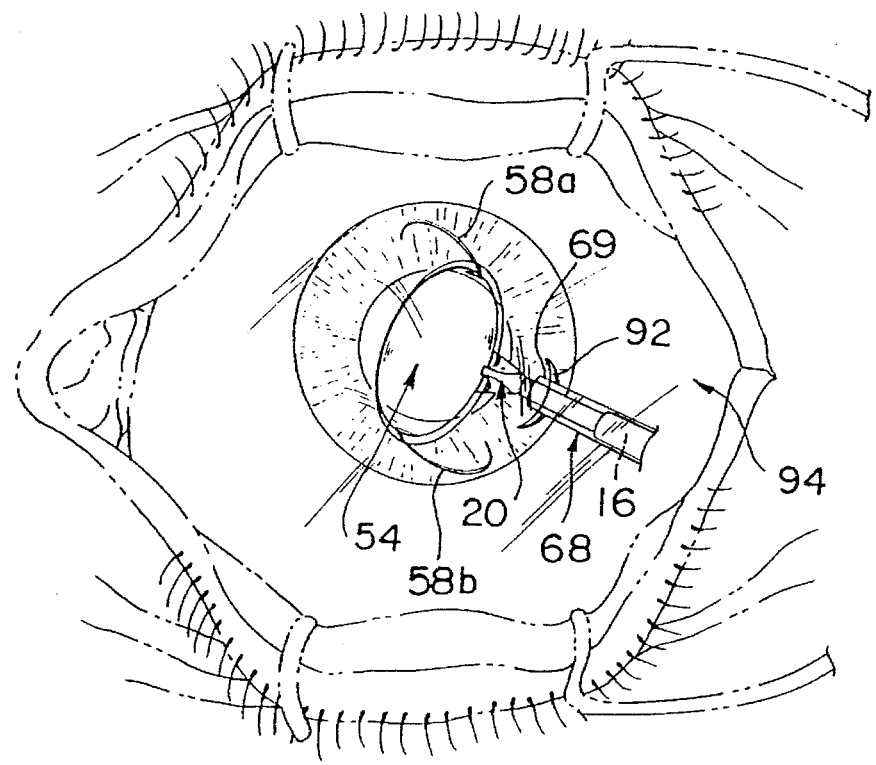
FIG. 27 is a perspective view showing the surgical implantation device positioning a deformable intraocular lens within the eye.

Suitable deformable intraocular lens for use in the present invention are shown in FIGS. 13–15. The deformable intraocular lens 54 shown in FIGS. 13 and 15 includes a lens body 56 with attachment means defined by a pair of haptics 58 each having one end anchored in the lens portion 56 and a free end for attachment to the eye tissue. The deformable intraocular lens 60 shown in FIG. 14 includes a lens body 62 and attachment means defined by a pair of lateral lobes 64 of the lens portion 62.

The details of the preferred lens holding microcartridge 12 are shown in FIGS. 16–20. The microcartridge 12 comprises a split tubular member 66 extending to a continuous tubular member 67 (i.e., "lens holding portion") and an implantation nozzle portion 68. When the microcartridge is in a closed position, a continuous circular or oval passageway of the same diameter extends through the split tubular member 66 through the continuous tubular member 67 and through the implantation nozzle portion 68. The microcartridge 12 is preferably made of injection molded plastic such as polypropylene. The split tubular member 66 is defined by a fixed portion 70 and a movable portion 72. The fixed portion 70 is fixed relative to the implantation nozzle portion 68, and is defined by a tubular portion 74 and extension 72. The movable portion 72 is movable relative to the fixed portion 70 for opening and closing the split tubular member 66. The movable portion 72 is defined by a tubular portion 78 and extension 80. A hinge 82 is provided between the fixed portion 70 and movable portion 72. The hinge 82 is defined by reducing the thickness of the walls of the tubular portion 74 and 75 at the hinge 82, as shown in FIGS. 17, 18 and 19. The hinge 82 runs the length of the split tubular member 66 to allow the extensions 76 and 78 to be split apart, or brought together to open and close, respectively, the split tubular member 66.

The tubular portion 78 of the movable portion 72 is provided with a sealing edge 84, which is exposed when the lens holding microcartridge 12 is opened, as shown in FIG. 16A, and seals with a similar sealing edge 86 (See FIGS. 17 and 21) of the continuous tubular member 67 when the lens holding microcartridge 12 is closed.

The end of the tip 69 is provided with three (3) equally spaced slots 87a, 87b and 87c of different length provided about the circumference thereof, as shown in FIGS. 20A and 20B. The slot 87a positioned at the top of the tip 69 is the shortest, slot 87c on the right side of the tip 20 is the longest, and slot 87b on the left side is of medium length. The slots 87a, 87b, 87c cause the lens 54 to rotate as it exits the tip 20.

Other embodiments of the microcartridge 12 according to the present invention are shown in FIGS. 30-33.

The microcartridge 12' shown in FIG. 30 is provided with a beveled tip 94 to facilitate entry of the tip through the incision in the eye during implantation. The beveled tip 94 can be set at approximately forty-five (45) degrees relative to the passageway through the microcartridge 12'.

The embodiment of the microcartridge 12' shown in FIGS. 31 and 32 is provided with a set of grooves 96 provided inside the passageway therethrough. The grooves accommodate the edges of the lens being loaded into the microcartridge to facilitate bending of the lens. Specifically, the edges of the lens are placed in the grooves 96 to prevent relative slippage of the edges with the inner surface of the passageway through the microcartridge when the microcartridge is being folded into the closed position.

The embodiments of the microcartridge shown in FIGS. 33A and 33B each have a tip 69' and 69" having an oval cross-section with slots 87" and 87" differently positioned as shown, respectively, again to facilitate entry through an incision in the eye. Alternatively, the cross-section can be two half circles set apart and connected together rather than oval.

Figure 44:
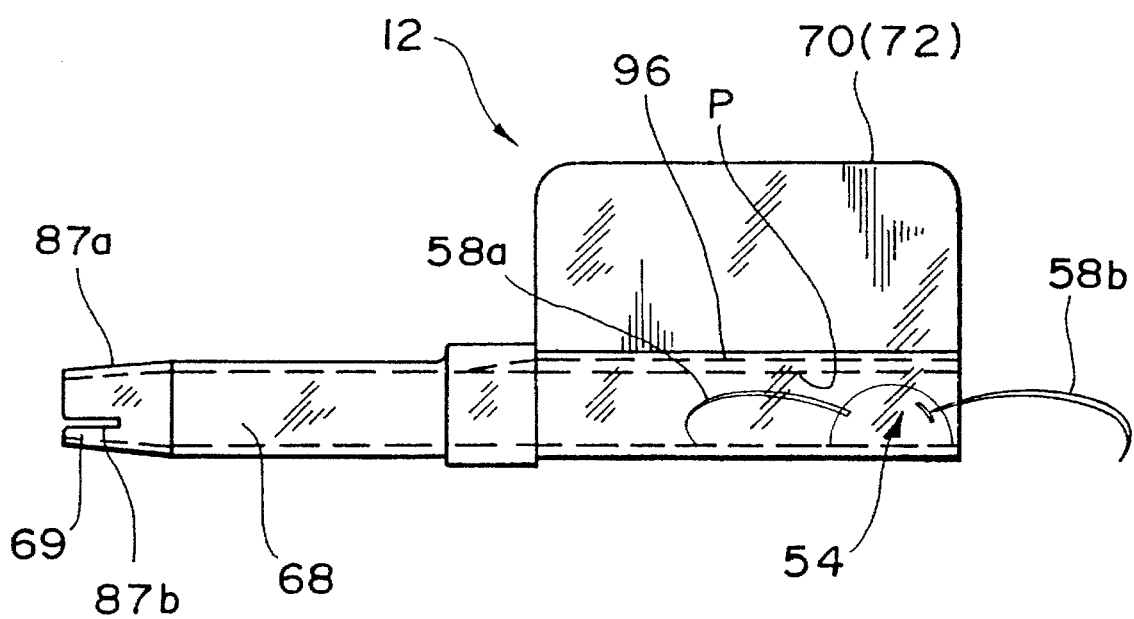
FIG. 44 is a side elevational view of a further alternative embodiment of the lens holding microcartridge provided with at least one groove in the passageway, an inwardly tapering passageway, and slots in the tip of the nozzle portion.

The various features of the microcartridges shown in FIGS. 16-21 and 30-33 can be used in various combinations to achieved an optimum design for a particular application. However, all of these features are typically considered improvements of the basic combination. For example, FIG. 44 shows a further embodiment which combines the features of at least one groove in the passageway, an inwardly tapering passageway, and slots in the tip of the nozzle portion.

The components of the device 10, except for the microcartridge 12, are preferably fabricated from autoclavable material such as stainless steel or from a disposable rigid plastic such as medical grade ABS or the like.

EMBODIMENTS WITH GROOVES/TAPERING PASSAGEWAY

Another embodiment of the present invention is shown in FIGS. 34-38. The lens microcartridge 100 comprises a lens holding portion 102 (FIG. 36) and a nozzle portion of 104. The lens microcartridge 100 is shown installed in a fixture 106 (e.g. end of surgical implantation device 10) in FIGS. 34 and 35. The fixture 106 is basically a cylinder with a slot 108 having tapered edges 110 for guiding the lens microcartridge 100 into the fixture 106.

The lens holding portion 102 is defined by a split tubular member including a fixed tubular portion 112 and a movable tubular portion 114. The fixed tubular portion 112 is provided with an extension 116 and the movable tubular portion 114 is provided with an extension 118.

The important features of this embodiment include alignment means for aligning the extensions 116 and 118 when the lens microcartridge 100 is closed, and means for tightly holding the lens microcartridge 100 closed when inserted in the fixture 106.

Figure 37:
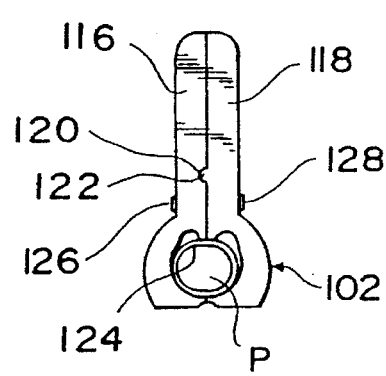
FIG. 37 is a rear end elevational view of the lens holding microcartridge shown in FIGS. 34 and 35, but removed from the lens injecting device.

An example of means for aligning the extensions 116 and 118 when the lens microcartridge 100 is closed is an alignment groove 120 cooperating with an alignment rib 122, as shown in FIG. 37. The alignment groove 120 and alignment rib 122 extend the length of the extensions 116 and 118, respectively. However, it is not necessary that the alignment groove 120 and alignment rib 122 run the entire length of the extensions 116 and 118, and can still be effective, if provided only for a portion of the length of the extensions.

Further, the extensions 116 and 118 can be aligned with other extension alignment means such as male/female alignment tabs, protrusions, surfaces, etc. Maintaining the alignment of the extensions 116 and 118 when the lens microcartridge is closed is important for maintaining the alignment of the movable tubular portion 114 relative to the fixed tubular portion 112. This alignment of the tubular portions maintains the inner seams of the extensions 116 and 118 inside the passageway 124 in alignment preventing exposed edges of these seams that can cause damage to the deformable intraocular lens during loading and/or insertion operations, particularly during the transition of the deformable intraocular lens from the lens holding portion into the nozzle portion during the insertion operation.

Means for tightly holding the lens microcartridge 100 closed when inserted in the fixture 106 can be provided by a variety of structural features of both the fixture 106 and/or lens microcartridge 100.

Due to the slot 108 configuration of the fixture 106, means for wedging the extensions 116 and 118 together provides an inexpensive and effective manner of achieving the desired function.

Figure 38:
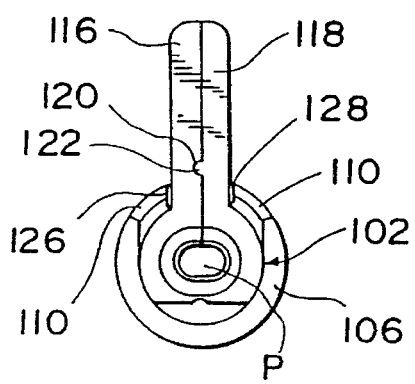
FIG. 38 is a rear end elevational view of the lens holding microcartridge inserted in a lens injecting device, as shown in FIGS. 34 and 35.

For example, the extensions 116 and 118 can be provided with protrusions 126 and 128, respectively, that cooperated with the edges of the slot 108 of the fixture 106, as shown in FIG. 38. The protrusions 126 and 128 serve as means for wedging the extensions 126 and 128 tightly between the edges of the slot 108 ensuring that the lens microcartridge is tightly held closed during the insertion operation. Further, the protrusions 126 and 128 again provide means for also aligning the extensions 116 and 118 providing the benefit described above with respect to alignment of the extension 126 and 128 to prevent damage to the intraocular lens.

The protrusions 126 and 128 resiliently, and possibly plastically deform to some extent during wedging utilizing the resilient properties of the plastic material of the lens microcartridge 100 to hold the lens holding portion 102 tightly closed and the extensions 116 and 118 accurately aligned.

The protrusions 126 and 128 can be in the form of strips, dots, squares or other shaped protrusions extending from the surfaces of the extensions 116 and 118.

Figure 39:
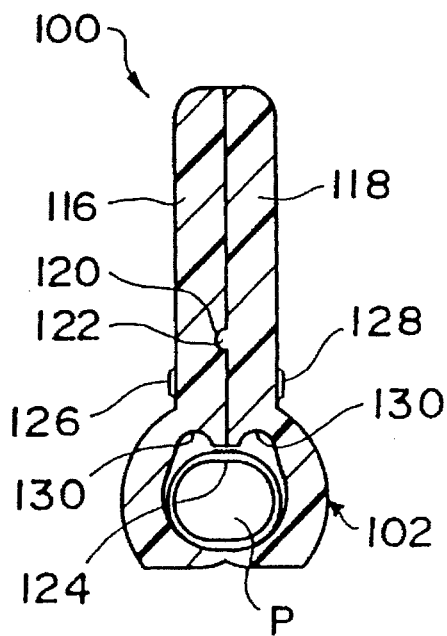
FIG. 39 is a cross-sectional view of the lens holding microcartridge as indicated at 39— 39 in FIG. 34.

In a preferred embodiment, the lens microcartridge 100 is provided with grooves 130 in the passageway 124, as shown in FIG. 39. The grooves 130 provide means for gripping the edges of the deformable intraocular lens during the lens folding operation.

The grooves 130 can be of constant depth and extend along the entire length of the lens holding portion 102. Alternatively, the grooves 130 can vary in depth and/or only extend a portion of the length of the lens holder 102. As a further alternative, the grooves 130 can also extend into the nozzle portion 104.

Figure 40:
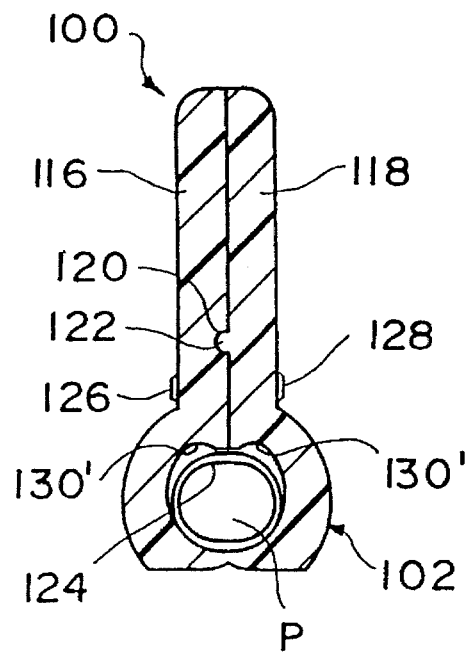
FIG. 40 is a cross-sectional view of the lens holding microcartridge as indicated at 40— 40 in FIG. 34.
Figure 41:
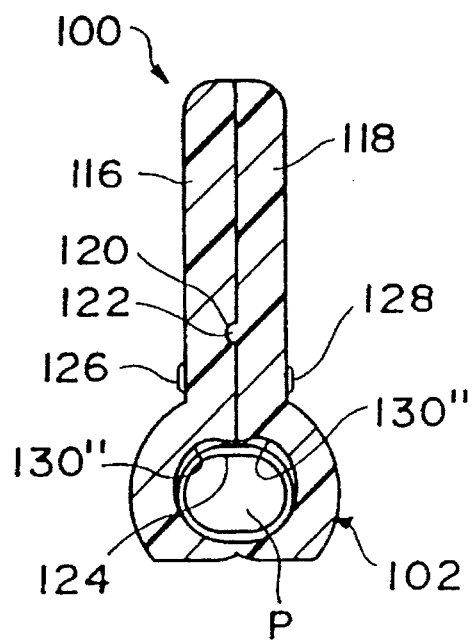
FIG. 41 is a cross-sectional view of the lens holding microcartridge as indicated at 41— 41 in FIG. 34.

In a preferred embodiment, the grooves taper from deeper depth grooves 130 as shown in the cross-sectional view in FIG. 39 to lesser depth grooves 130', as shown in FIG. 40, and even lesser depth grooves 130", as shown in FIG. 41, respectively. This tapering configuration of the grooves 130 enables the deformable intraocular lens to transition smoothly without damage thereto from the lens holder portion 102 into the nozzle portion 104.

Figure 42:
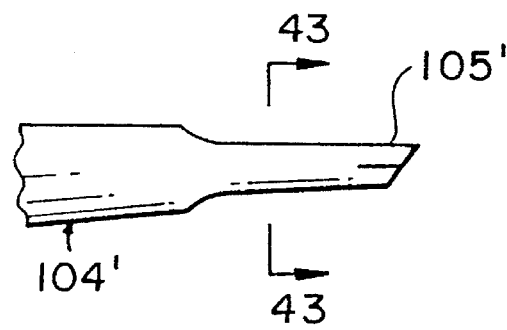
FIG. 42 is a side elevational view of a lens holding microcartridge according to the present invention with a heat deformed and beveled tip.
Figure 43:
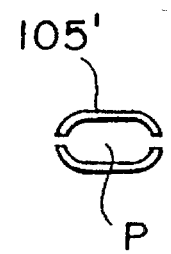
FIG. 43 is a cross-sectional view of the tip as indicated at 43—43 in FIG. 42.

Another embodiment of the tip portion 104' for the microcartridge according to the present invention is shown in FIG. 42. The nozzle portion 104' is provided with a heat deformed tip for increasing the strength and reducing the cross section of the tip to facilitate insertion through a smaller incision. The heat deformed tip allows for much higher resistance to rupture than a non-heat treated tip. Further, the tip portion 104' is beveled and provided with an oval shaped cross section, as shown in FIG. 43.

METHODS OF IMPLANTATION

The surgical procedure begins by coating the lens with a surgically compatible lubricant, and loading the lens into the microcartridge. For example, as shown in FIG. 21, a lens 54 having a lens body 56, a leading haptic 58a is loaded into the microcartridge 12 while a trailing haptic 58b remains trailing outside the microcartridge in the manner shown. Specifically, the lens 54 is loaded downwardly into the opened microcartridge 12 until it sits on the inner surfaces of the tubular portions 74 and 78, for example, with a pair of tweezers. The outer circumferential surface edges of the lens 54 are held by edges 88 and 90 of the tubular portions 74 and 78, respectively. The rear edge of the lens 54 is placed approximately at the rear edge of the microcartridge 12. The lens 54 is further manipulated to situate the haptics 58a and 58b in the manner shown. Specifically, haptic 54a is positioned in a leading position and the other haptic 54b is positioned in a trailing position outside the microcartridge 12 with respect to the direction of implantation, as indicated by the arrow.

Subsequently, the split tubular member 66 of the microcartridge 12 is closed about the lens 54 by forcing the extensions 76 and 80 together with his or her finger tips. The inner surfaces of the tubular portions 74 and 78 bend and fold the lens 54 when the extensions 76 and 80 are forced together, as shown in FIGS. 22 and 23. Due to the resilient nature of the deformable intraocular lens 54, the lens 54 conforms to the curved inner surfaces of the tubular portions 74 and 78 without damage thereto, as shown in FIG. 23.

The microcartridge 12 containing the loaded lens 54 is inserted between the edges 17a, 17a of the opening 17 into the lens cartridge receiver 15 of the lens injecting device 13. As the microcartridge 12 is moved forward, the extensions 76 and 80 move past the tapered edges 17b, 17b and come to a stop position between the clamping edges 17c, 17c when front portions of the extensions 76 and 80 contact with the stop edge 17d. The clamping edges 17c prevent rotation of the microcartridge 12 inside the lens injecting device 13.

The user pushes the threaded end cap 18 forward while securing the body 14 of the lens injecting device 13 from movement, forcing the plunger 16 forward within the lens injecting device 13. As the plunger 16 is moved forward, the tip 20 enters into the rear of the microcartridge 12 and misses the trailing haptic 58B until the tip makes contact with the loaded lens 54, as shown in FIG. 24. As the plunger 16 is moved forward in this manner, the lens 54 previously lubricated, is forced into the implantation nozzle portion 68 of the microcartridge 12, as shown in FIG. 25.

Once the lens 54 enters the implantation nozzle portion 68, the threads of the end cap 18 contact with the threads of the sleeve 24 stopping further movement of the plunger 14 forward in this manner. The end cap 18 is slightly rotated to engage the threads of the end cap 18 with the threads of the sleeve 24. At this point, the surgical device is ready for the implantation step. The tip 69 of the nozzle portion 68 is insert through the incision in the eye, and the end cap 18 is rotated to continue the forward movement of the plunger 16 by continued rotation of the end cap 18 relative to the holder body 14 to expel the lens from the nozzle into the interior of the eye, as shown in FIG. 26. This manner of screw advancement for moving the plunger 16 forward provides for precise control and accuracy concerning forcing the lens 54 through the remaining portion of the tip 69 into the eye during the implantation procedure. The deformed lens after exiting the nozzle portion 68 returns to its original configuration, full size and fixed focal length.

Figure 28:
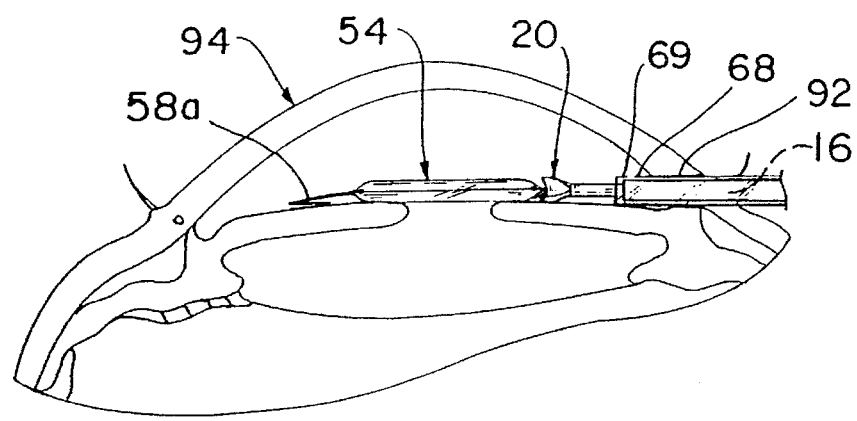
FIG. 28 is a cross-sectional view of an eye showing the positioning of the deformable intraocular lens into position in the eye by the surgical device.
Figure 34:
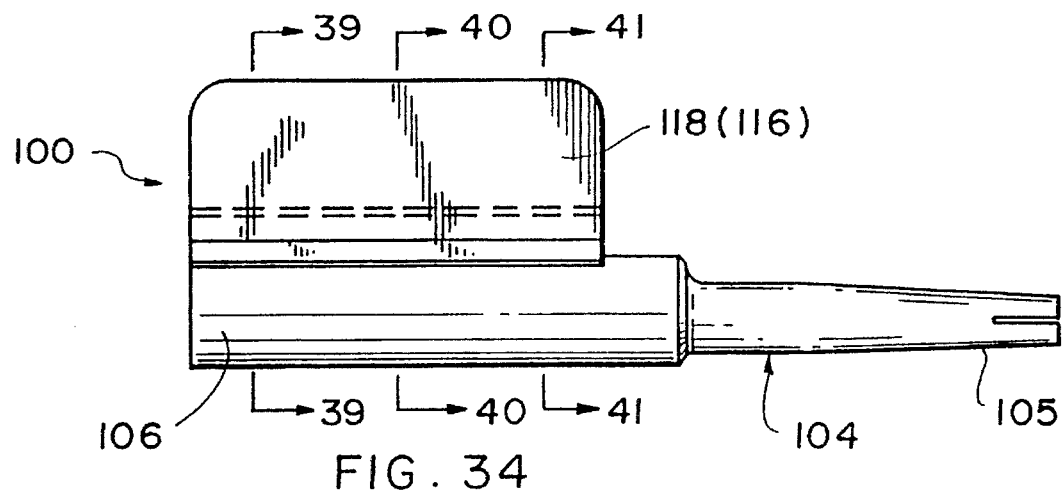
FIG. 34 is a side elevational view of another embodiment of the lens holding microcartridge according to the present invention inserted in a lens injecting device.
Figure 35:
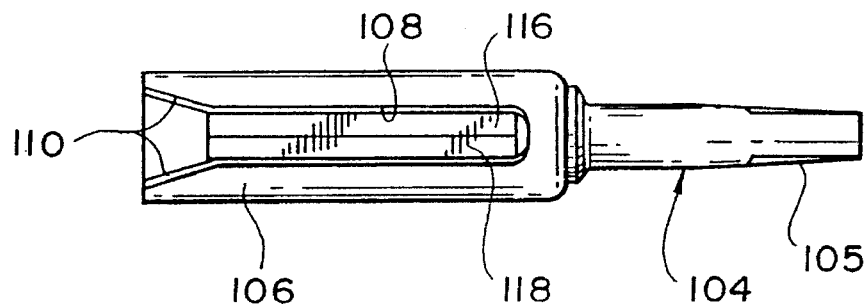
FIG. 35 is a top planar view of the lens holding microcartridge inserted in a lens injecting device, as shown in FIG. 34.
Figure 36:
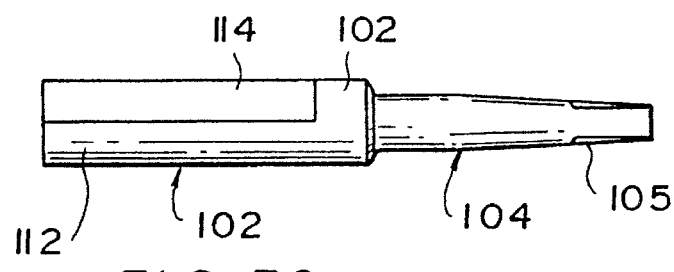
FIG. 36 is a bottom planar view of the lens holding microcartridge shown in FIGS. 34 and 35, but removed from the lens injecting device.

After the lens is inserted into the eye, the end cap 18 is further rotated to fully expose the tip 20 of the plunger 16, as shown in FIGS. 28 and 29, to allow the lens to be pushed forward, side manipulated to rotate the lens, and pushed down to properly position the lens within the eye without the aid of other surgical instruments.

The configuration of the tip 20 is important during the implantation process. The faceted tip 20 provides a clearance between the tip 20 and the inner surface of the passageway through the microcartridge 12 to accommodate the trailing haptic 58b during movement of the lens within the microcartridge 12, as shown in FIGS. 25 and 26. Specifically, there exists a sufficient clearance between the flat surface facet 44 and the inner wall of the passageway through the microcartridge 12. During the implantation process, the trailing haptic 58b floats around in the space between the extension 42 of the tip 20 and the inner wall of the passageway, as shown in FIG. 25. This prevents any chance of damage to the trailing haptic 58b, for example, by being caught between the tip 20 and the lens 54 during the implantation process. The leading haptic 58a moves through the passageway unimpeded during the implantation process preventing any damage thereto.

I claim:

1. A lens cartridge for use in a surgical lens inserting device for implantation of a deformable intraocular lens into the eye through a relatively small incision made in the ocular tissue, said lens cartridge comprising:

a lens holding portion; and a nozzle portion connected to and extending from said lens holding portion, said lens holding portion and said nozzle portion having a passageway extending therethrough, said passageway having at least one groove extending along at least a portion of the length of said passageway, wherein the lens cartridge is configured to be accommodated in the surgical lens inserting device and a tip of said nozzle portion is to be inserted through the relatively small incision made in the ocular tissue for insertion of the deformable intraocular lens into the eye.

2. A lens cartridge according to claim 1, wherein said at least one groove is located in a portion of said passageway extending through said lens holding portion of the lens cartridge.

3. A lens cartridge according to claim 2, wherein said portion of said passageway having said at least one groove transitions to a groove-less portion of said passageway extending through said nozzle portion.

4. A lens cartridge according to claim 3, wherein at least a portion of said passageway tapers inwardly in a direction of insertion of the deformable intraocular lens.

5. A lens cartridge according to claim 4, wherein said inwardly tapering portion of said passageway is located in said nozzle portion.

6. A lens cartridge according to claim 2, wherein said at least one groove ends before a distal end of said nozzle portion.

7. A lens cartridge according to claim 6, wherein at least a portion of said passageway tapers inwardly in a direction of insertion of the deformable intraocular lens.

8. A lens cartridge according to claim 7, wherein said inwardly tapering portion of said passageway is located in said nozzle portion.

9. A lens cartridge according to claim 2, wherein at least a portion of said passageway tapers inwardly in a direction of insertion of the deformable intraocular lens.

10. A lens cartridge according to claim 9, wherein said inwardly tapering portion of said passageway is located in said nozzle portion.

11. A lens cartridge according to claim 1, wherein said at least one groove comprises a set of opposed grooves extending along at least a portion of the length of said passageway.

12. A lens cartridge according to claim 11, wherein said set of opposed grooves are located above a horizontal centerplane of said passageway.

13. A lens cartridge according to claim 12, wherein said set of opposed grooves are provided adjacent to each other.

14. A lens cartridge according to claim 11, wherein said set of opposed grooves are provided adjacent to each other.

15. A lens cartridge according to claim 11, wherein at least a portion of said passageway tapers inwardly in a direction of insertion of the deformable intraocular lens.

16. A lens cartridge according to claim 15, wherein said inwardly tapering portion of said passageway is located in said nozzle portion.

17. A lens cartridge according to claim 1, wherein said at least one groove varies in depth between said lens holding portion and said nozzle portion.

18. A lens cartridge according to claim 17, wherein at least a portion of said passageway tapers inwardly in a direction of the deformable intraocular lens.

19. A lens cartridge according to claim 18, wherein said inwardly tapering portion of said passageway is located in said nozzle portion.

20. A lens cartridge according to claim 1, wherein said passageway is continuous.

21. A lens cartridge according to claim 1, wherein at least a portion of said passageway is inwardly tapering in a direction of insertion of the deformable intraocular lens.

22. A lens cartridge according to claim 1, wherein said inwardly tapering portion of said passageway is located in said nozzle portion.

23. A lens cartridge according to claim 1, wherein said nozzle portion includes a beveled end for facilitating entry of the nozzle portion through the incision in the ocular tissue.

24. A lens cartridge according to claim 1, wherein said lens cartridge is configured to open for loading the deformable intraocular lens into said lens cartridge, and closed for inserting said lens cartridge into the surgical lens inserting device for insertion of the deformable intraocular lens.

25. A lens cartridge according to claim 24, wherein said lens cartridge is configured to deform the deformable intraocular lens when closing to condense the configuration of the deformable intraocular lens to pass through said passage in said nozzle portion for inserting the lens through the incision in the ocular tissue.

26. A lens cartridge according to claim 25, wherein the deformable intraocular lens is placed into a curved folded configuration within said passageway in said lens cartridge leading to said nozzle portion when said lens holder portion is closed.

27. A lens cartridge according to claim 26, wherein said lens holder portion comprises a split tubular member defining a portion of said passageway and connected to said nozzle portion, said split tubular member can be opened to insert the deformable intraocular lens and closed to insert the lens cartridge into the surgical lens inserting device for insertion of the deformable intraocular lens.

28. A lens cartridge according to claim 27, wherein said split tubular member is defined by a fixed tubular portion and a movable tubular portion connected together at a hinge, and said fixed tubular portion is connected to said nozzle portion while said movable tubular portion moves relative to said nozzle portion.

29. A lens cartridge according to claim 28, wherein said hinge is defined by a decrease in wall thickness at a joint between said fixed tubular portion and said movable tubular portion.

30. A lens cartridge according to claim 28, wherein said fixed tubular portion includes an extension and said movable tubular portion includes an extension, said extensions are moved apart to open said lens holding portion for loading the deformable intraocular lens and moved together to fold the deformable intraocular lens and close said lens holding portion for inserting the lens cartridge into the surgical lens inserting device for insertion of the deformable intraocular lens.

31. A lens cartridge according to claim 1, wherein the lens cartridge is made of disposable surgically acceptable plastic.

32. A lens cartridge according to claim 1, wherein a cross section of said nozzle portion is selected from the group consisting of circular, oval and two half circles set apart and connected together.

33. A lens cartridge according to claim 1, wherein a tip of said nozzle portion is provided with slots for allowing expansion of said passageway.

34. A lens cartridge according to claim 1, wherein said lens holding portion and said nozzle portion have a one-piece construction.

35. A lens microcartridge according to claim 1, wherein said nozzle portion is provided with a heat deformed tip for increasing the strength and reducing the cross section of the tip to facilitate insertion through a smaller incision.

36. A lens cartridge for use in a surgical lens inserting device for implantation of a deformable intraocular lens into the eye through a relatively small incision in the ocular tissue, said lens cartridge comprising:

a lens holding portion; and a nozzle portion connected to and extending from said lens holding portion, said lens holding portion and said nozzle portion having an inwardly tapering passageway of decreasing cross-sectional size extending therethrough for further folding or compressing the deformable intraocular lens when moving through said inwardly tapering passageway, wherein the lens cartridge is configured to be accommodated in the lens inserting device and a tip of said nozzle portion is to be inserted through the relatively small incision in the ocular tissue for insertion of the deformable intraocular lens into the eye.

37. A lens cartridge according to claim 36, wherein only a portion of said passageway is an inwardly tapering passageway portion.

38. A lens cartridge according to claim 37, wherein said inwardly tapering passageway portion is located in said nozzle portion.

39. A lens cartridge according to claim 43, wherein said at least one groove is configured for further folding the deformable intraocular lens when moving through said passageway.

40. A lens cartridge according to claim 41, wherein said at least one groove is configured for further folding the deformable intraocular lens when moving through said passageway.

41. A lens cartridge according to claim 37, wherein said passageway is provided with at least one groove extending along at least a portion of the length of said passageway.

42. A lens cartridge according to claim 41, wherein said at least one groove is located in a portion of said passageway extending through said lens holding portion of the lens cartridge.

43. A lens cartridge according to claim 36, wherein said passageway is provided with at least one groove extending along at least a portion of the length of said passageway.

44. A lens cartridge according to claim 43, wherein said at least one groove is located in a portion of said passageway extending through said lens holding portion of the lens cartridge.

45. A lens cartridge according to claim 44, wherein said portion of said passageway having said at least one groove transitions to a groove-less portion of said passageway extending through said nozzle portion.

46. A lens cartridge according to claim 44, wherein said at least one groove ends before a distal end of said nozzle portion.

47. A lens cartridge according to claim 43, wherein said at least one groove comprises a set of opposed grooves extending along at least a portion of the length of said passageway.

48. A lens cartridge according to claim 43, wherein said at least one groove varies in depth in a direction along the length of said passageway.

49. A lens cartridge according to claim 43, wherein said passageway is continuous.

50. A lens cartridge for use in a surgical lens inserting device for manipulation of a deformable intraocular lens into the eye through a relatively small incision made in the ocular tissue, said lens cartridge comprising:
   a lens holding portion; and
   a nozzle portion connected to and extending from said lens holding portion, said lens holding portion and said nozzle portion having a passageway extending therethrough, said passageway having at least one inwardly tapering groove for folding the deformable intraocular lens,
   wherein the lens cartridge is configured to be accommodated in the lens injecting device and a tip of said nozzle portion is to be inserted through the relatively small incision in the ocular tissue for insertion of the deformable intraocular lens into the eye.

51. A lens cartridge according to claim 50, wherein said at least one inwardly tapering groove is located in a portion of said passageway extending through said lens holding portion.

52. A lens cartridge according to claim 51, wherein said portion of said passageway having said inwardly tapering groove transitions to a groove-less portion of said passageway extending through said nozzle portion.

53. A lens cartridge according to claim 50, wherein said at least one inwardly tapering groove comprises a set of opposed inwardly tapering grooves extending along at least a portion of the length of said passageway for continuously folding edges of the deformable intraocular lens inwardly.

54. A lens cartridge according to claim 50, wherein a portion of said passageway extending through said nozzle portion is an inwardly tapering passageway portion.

55. A lens cartridge according to claim 50, wherein said lens holding portion is defined by a split tubular member having a fixed tubular portion fixed relative to said nozzle portion and a movable tubular portion movable relative to said nozzle portion for opening and closing the lens cartridge, and said split tubular member including alignment means for aligning said movable tubular member with said fixed tubular member upon closing the lens cartridge.

56. A lens cartridge according to claim 55, further comprising one extension connected to said fixed tubular member and another extension connected to said movable tubular member, said alignment means being part of said extensions.

57. A lens cartridge according to claim 56, wherein said alignment means is defined by an alignment rib on one said extension cooperating with a groove in the other said extension.

* * * * *